US00PP30221P2

(12) United States Plant Patent
Oliver

(10) Patent No.: US PP30,221 P2
(45) Date of Patent: Feb. 19, 2019

(54) ***PHLOX* PLANT NAMED 'ROSE BOUQUET'**

(50) Latin Name: *Phlox carolina*
Varietal Denomination: Rose Bouquet

(71) Applicant: Charles G. Oliver, Scottdale, PA (US)

(72) Inventor: Charles G. Oliver, Scottdale, PA (US)

( * ) Notice: Subject to any disclaimer, the term of this patent is extended or adjusted under 35 U.S.C. 154(b) by 0 days.

(21) Appl. No.: 15/731,897

(22) Filed: Aug. 21, 2017

(51) Int. Cl.
*A01H 5/02* (2018.01)

(52) U.S. Cl.
USPC ..... Plt./320

(58) Field of Classification Search
USPC ..... Plt./320
See application file for complete search history.

*Primary Examiner* — Keith O. Robinson
(74) *Attorney, Agent, or Firm* — C. A. Whealy

(57) ABSTRACT

A new and distinct *Phlox* plant named 'Rose Bouquet', characterized by its compact, upright and mounding plant form; vigorous growth habit and rapid growth rate; freely basal branching habit; dense and full plants; early and freely flowering habit; large inflorescences with light red purple-colored flowers; and resistance to Powdery Mildew.

2 Drawing Sheets

Botanical designation: *Phlox carolina.*
Cultivar denomination: 'ROSE BOUQUET'.

BACKGROUND OF THE INVENTION

The present invention relates to a new and distinct *Phlox* plant, botanically known as *Phlox carolina* and hereinafter referred to by the name 'Rose Bouquet'.

The new *Phlox* plant is a product of a planned breeding program conducted by the Inventor in Upper Tyrone Township, Pa. The objective of the breeding program is to create new vigorous *Phlox* plants with early flowering habit, attractive leaf and flower coloration and resistance to Powdery Mildew.

The new *Phlox* plant originated from a cross-pollination conducted by the Inventor in May, 2013 of *Phlox carolina* 'Minnie Pearl', not patented, as the female, or seed, parent with *Phlox carolina* 'Kim', not patented, as the male, or pollen, parent. The new *Phlox* plant was discovered and selected by the Inventor as a single flowering plant within the progeny of the stated cross-pollination in a controlled environment in Upper Tyrone Township, Pa. in June, 2014.

Asexual reproduction of the new *Phlox* plant by vegetative stem cuttings in a controlled greenhouse environment in Upper Tyrone Township, Pa. since September, 2014 has shown that the unique features of this new *Phlox* plant are stable and reproduced true to type in successive generations.

SUMMARY OF THE INVENTION

Plants of the new *Phlox* plant have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Rose Bouquet'. These characteristics in combination distinguish 'Rose Bouquet' as a new and distinct *Phlox* plant:

1. Compact, upright and mounding plant form.

2. Vigorous growth habit and rapid growth rate.
3. Freely basal branching habit; dense and full plants.
4. Early and freely flowering habit.
5. Large inflorescences with light red purple-colored flowers.
6. Resistance to Powdery Mildew.

Plants of the new *Phlox* differ from plants of the female parent, 'Minnie Pearl', in the following characteristics:

1. Plants of the new *Phlox* are more compact than plants of 'Minnie Pearl'.
2. Plants of the new *Phlox* have shorter internodes and are denser than and not as open as plants of 'Minnie Pearl'.
3. Plants of the new *Phlox* are more freely branching than plants of 'Minnie Pearl'.
4. Inflorescences of plants of the new *Phlox* are taller than and have more flowers than inflorescences of plants of 'Minnie Pearl'.
5. Plants of the new *Phlox* flower for a longer period of time than plants of 'Minnie Pearl'.
6. Plants of the new *Phlox* and 'Minnie Pearl' differ in flower color as plants of 'Minnie Pearl' have white-colored flowers.

Plants of the new *Phlox* differ from plants of the male parent, 'Kim', in the following characteristics:

1. Plants of the new *Phlox* are more freely flowering than plants of 'Kim'.
2. Plants of the new *Phlox* flower for a longer period of time than plants of 'Kim'.
3. Plants of the new *Phlox* have larger flowers than plants of 'Kim'.

Plants of the new *Phlox* can be compared to plants of *Phlox* x *hybrida* 'Aurora', disclosed in U.S. Plant Pat. No. 27,264. In side-by-side comparisons, plants of the new *Phlox* and 'Aurora' differ in the following characteristics:

1. Plants of the new *Phlox* are more compact than plants of 'Aurora'.
2. Plants of the new *Phlox* are more freely flowering than plants of 'Aurora'.
3. Plants of the new *Phlox* flower for a longer period of time than plants of 'Aurora'.

4. Plants of the new *Phlox* have larger flowers than plants of 'Aurora'.
5. Plants of the new *Phlox* and 'Aurora' differ in flower color as plants of 'Aurora' have white and pink-colored flowers.

Plants of the new *Phlox* can also be compared to plants of *Phlox carolina* X *Phlox maculata* 'Zenith', disclosed in U.S. Plant Pat. No. 27,266. In side-by-side comparisons, plants of the new *Phlox* and 'Zenith' differ in the following characteristics:

1. Plants of the new *Phlox* are more compact than plants of 'Zenith'.
2. Plants of the new *Phlox* are more freely flowering than plants of 'Zenith'.
3. Plants of the new *Phlox* flower for a longer period of time than plants of 'Zenith'.
4. Plants of the new *Phlox* and 'Zenith' differ in flower color as plants of 'Zenith' have pink-colored flowers.

BRIEF DESCRIPTION OF THE PHOTOGRAPHS

The accompanying colored photographs illustrate the overall appearance of the new *Phlox* plant showing the colors as true as it is reasonably possible to obtain in colored reproductions of this type. Colors in the photographs may differ slightly from the color values cited in the detailed botanical description which accurately describe the colors of the new *Phlox* plant.

The photograph on the first sheet comprises a side perspective view of typical flowering plants of 'Rose Bouquet' grown in a container.

The photograph on the second sheet is a close-up view of a typical flowering plant of 'Rose Bouquet'.

DETAILED BOTANICAL DESCRIPTION

The aforementioned photographs and following observations, measurements and values describe plants grown during the spring and early summer in one-gallon containers in a polyethylene-covered greenhouse in Upper Tyrone Township, Pa. and under cultural practices typical of *Phlox* production. During the production of the plants, day temperature ranged from 15° C. to 26° C. and night temperatures ranged from 5° C. to 15° C. Plants were two years old when the photographs and description were taken. In the following description, color references are made to The Royal Horticultural Society Colour Chart, 1995 Edition, except where general terms of ordinary dictionary significance are used.

Botanical classification: *Phlox carolina* 'Rose Bouquet'.

Parentage:

*Female, or seed, parent.*—*Phlox carolina* 'Minnie Pearl', not patented.

*Male, or pollen, parent.*—*Phlox carolina* 'Kim', not patented.

Propagation:

*Type.*—By stem cuttings.

*Time to initiate roots, summer.*—About three weeks at night temperatures about 15° C. and day temperatures about 26° C.

*Time to produce a rooted plant, summer.*—About six weeks at night temperatures about 15° C. and day temperatures about 26° C.

*Root description.*—Medium in thickness, fibrous; white in color.

*Rooting habit.*—Freely branching; medium density.

Plant description:

*Plant and growth habit.*—Herbaceous perennial; compact, upright and mounding plant habit; vigorous growth habit; rapid growth rate; relatively short internodes; freely basal branching habit with about 30 to 40 lateral branches developing per plant; dense and full appearance.

*Plant height.*—About 35 cm.

*Plant width (spread).*—About 30 cm.

*Lateral branches.*—Length: About 35 cm. Diameter: About 1.5 mm. Internode length: About 1.5 cm to 6 cm. Strength: Strong. Aspect: Mostly upright. Texture: Slightly pubescent. Color: Close to 145A; under high light conditions, close to 58A.

Leaf description:

*Arrangement.*—Opposite, simple; sessile.

*Length.*—About 4 cm to 9.5 cm.

*Width.*—About 0.5 cm to 2 cm.

*Shape.*—Lanceolate.

*Apex.*—Acute.

*Base.*—Gradually tapering.

*Margin.*—Entire.

*Texture and luster, upper and lower surfaces.*—Smooth, glabrous; matte.

*Venation pattern.*—Pinnate.

*Color.*—Developing leaves, upper and lower surfaces: Close to 138B. Fully expanded leaves, upper surface: Close to 137A; venation, close to 137A. Fully expanded leaves, lower surface: Close to 138B; venation, close to 138B.

Flower description:

*Flower form and flowering habit.*—Single rotate and salverform flowers arranged in dense terminal compound panicles; panicles rounded in shape; freely flowering habit with about 80 to 120 flowers developing per inflorescence; flowers face upright to outwardly.

*Fragrance.*—Moderately fragrant; sweet.

*Natural flowering season.*—Early flowering habit, plants begin flowering about six weeks after planting; relatively long flowering period with plants flowering continuously from mid-spring to mid-summer in Pennsylvania.

*Postproduction longevity.*—Flowers last about five days on the plant; flowers not persistent.

*Flower buds.*—Height: About 2.6 cm. Diameter: About 4 mm. Shape: Torch-shaped. Color: Close to 74D.

*Inflorescence height.*—About 10 cm.

*Inflorescence diameter.*—About 10 cm.

*Flower diameter.*—About 3 cm.

*Flower depth.*—About 3.2 cm.

*Flower throat diameter.*—About 2 mm.

*Flower tube length.*—About 3.2 cm.

*Flower tube diameter, at base.*—About 1.5 mm.

*Petals.*—Quantity per flower and arrangement: Typically five in a single whorl; petals fused at the base into a narrow tube. Lobe length: About 1.4 cm. Lobe width: About 1.2 cm. Shape: Rhomboidal. Apex: Obtuse. Margin: Entire. Texture and luster: Petal lobes, upper and lower surfaces: Smooth, glabrous; matte. Throat: Smooth, glabrous; matte. Tube: Smooth, glabrous; matte Color: Developing and fully expanded petal lobes, upper surface: Close to 74C; venation, close to 74C; color does not change with development. Developing and fully expanded petal lobes, lower surface: Close to 75C; venation, close to 75C; color does not change with development. Flower throat: Close to 75D; venation, close to 75D. Flower tube: Close to 75D; venation, close to 75D.

*Sepals*.—Quantity per flower and arrangement: Cylindrical calyx with five sepals in a single whorl, fused towards the base. Length: About 1 cm. Width: About 1.2 mm. Shape: Lanceolate. Apex: Acute. Margin: Entire, membraneous. Texture, upper and lower surfaces: Smooth, glabrous. Color, upper and lower surfaces: Close to 145B.

*Peduncles*.—Length: About 3.5 cm. Diameter: About 1.5 mm. Angle: Erect. Strength: Strong. Texture: Pubescent. Color: Close to 145A.

*Pedicels*.—Length: About 3 mm to 5 mm. Diameter: About 1 mm. Angle: About 30° from peduncle axis. Strength: Strong. Texture: Slightly pubescent. Color: Close to 145A.

*Reproductive organs*.—Stamens: Quantity per flower: Typically five. Filament length: About 1 mm. Filament color: Close to 154D. Anther shape: Oval. Anther size: About 1.8 mm by 0.6 mm. Anther color: Close to 17A. Pollen amount: Abundant. Pollen color: Close to 17A. Pistils: Quantity per flower: One. Pistil length: About 2.2 cm. Stigma shape: Tri-parted. Stigma color: Close to 154C. Style length: About 1.9 cm. Style color: Close to 154D. Ovary color: Close to 145B.

*Seeds*.—Seed development has not been observed on plants of the new *Phlox* to date.

Disease & pest resistance: Plants of the new *Phlox* have been observed to be resistant to Powdery Mildew (*Erysiphe cichoracearum*). Plants of the new *Phlox* have not been observed to be resistant to pests and other pathogens common to *Phlox* plants.

Garden performance: Plants of the new *Phlox* have been observed to have good garden performance and tolerate rain and wind and to temperatures ranging from about −30° C. to 45° C.

It is claimed:

1. A new and distinct *Phlox* plant named 'Rose Bouquet' as illustrated and described.

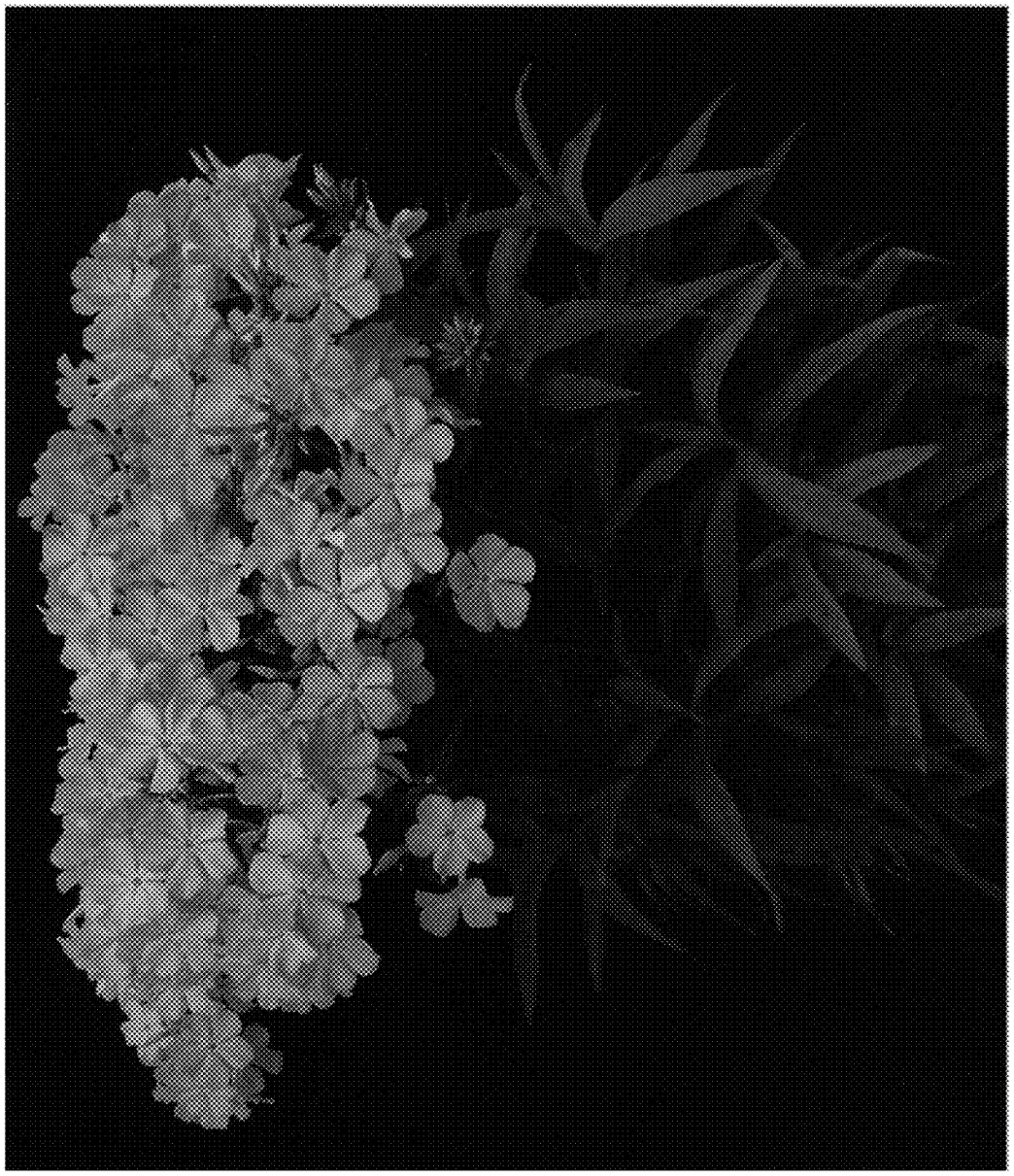

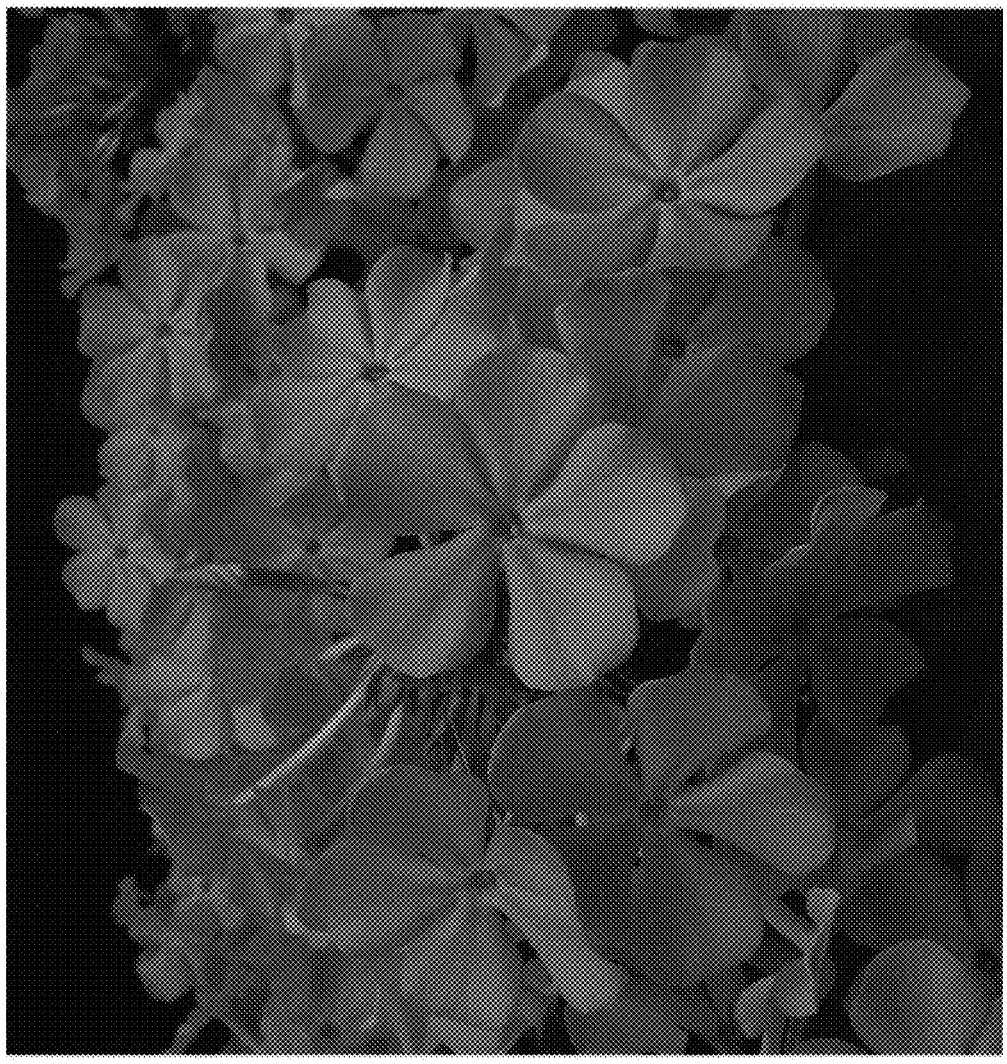

* * * * *